United States Patent [19]

Hierholzer

[11] Patent Number: 5,262,359
[45] Date of Patent: Nov. 16, 1993

[54] METHOD OF PROPAGATING HUMAN PARAMYXOVIRUSES USING CONTINUOUS CELL LINES

[75] Inventor: John C. Hierholzer, Atlanta, Ga.

[73] Assignee: The United States of America, as represented by the Secretary, Dept. of HHS, Washington, D.C.

[21] Appl. No.: 611,088

[22] Filed: Nov. 9, 1990

[51] Int. Cl.$^5$ .......................... C12N 7/00; C12N 7/06; C12N 7/02
[52] U.S. Cl. .................................. 435/235.1; 435/239
[58] Field of Search .......................... 435/235.1, 239

[56] References Cited

U.S. PATENT DOCUMENTS 4,188,375 2/1980 Straub .................................. 424/88

OTHER PUBLICATIONS

Reigel. J. of Virological Methods, vol. 12, 1985, pp. 323-327.
Carney et al. Cancer Research, vol. 45, 1985, pp. 2913-2923.
Morivch: et al. J. of Clinical Microbiology, vol. 28(6) 1990 pp. 1147-1150.
"Diagnostic Procedure for Viral and Rickettsial Diseases", 3rd Edition, by Edwin H. Lennette, M.D., Ph.D. and Nathalie J. Schmidt, Ph.D., Published by American Public Health Association, Inc., 1964, pp. 474, 475, 495.
"Basic Medical Virology", 1966 by James E. Prier, Ph.D., pp. 263, 272.
Diagnostic Procedures for: Viral, Rickettsial and Chlamydial Infections, 5th Edition, Edwin H. Lennette, Nathalie J. Schmidt, Editors, 1979, pp. 618-619 and 641.
Viral and Rickettsial Infections of Man, by Frank L. Horsfall, Jr., M.D., Fourth Edition, pp. 749-750, 757, 762.
Archives of Virology, Contents, vol. 115 No. 3-4, Published Dec. 13, 1990, by E. Castells, V. G. George and J. C. Hierholzer.
Frank et al., Comparison of Different Tissue Cultures for Isolation and Quantitation of Influenza and Parainfluenza Viruses, Journal of Clinical Microbiology, 10:32-36 (1979).
Itoh et al., Viral Susceptibility of an African Green Monkey Kidney Cell Line-Vero, Wirisu, 18:214-28 (1968).
Itoh et al., Effect of Tyrpsin on Viral Susceptibility of Vero Cell Cultures—Cercopithecus Kidney Line; Japan. J. Med. Sci. Biol, 23:227-35 (1970).
Komada et al., Isolation and Characterization of Monoclonal Antibodies to Human Parainfluenza Virus Type 4 and their Use in Revealing Antigenic Relation between Subtypes 4A and 4B, Virology, 171:28-37 (1989).
Macfarlane et al., VERO Cells (Cercopithecus Aethiops Kidney)—Growth Characteristics and Viral Susceptibility for Use in Diagnostic Virology, Archiv fur die gesamte Virusforschung, 27:379-86 (1969).
Morimoto et al., Effect of Trypsin of Reproduction of Type 4 Parainfluenza Virus in Vero Cell Cultures Under Fluid Overlay, Japan. J. Med. Sci. Biol., 23:1-11 (1970).
Okawa et al., Attempts at Adaptation of Parainfluenza Type 1 (HA-2) Virus to Vero Cell Cultures-Cercopithecus Kidney Line; Wirisu, 20:15-22 (1970).
Castells et al., NCI-H292 as an Alternative Cell Line for the Isolation and Propagation of the Human Paramyxoviruses, Arch. Virol., 115:277-88 (1990).
ASM Abstract #367, Anaheim, Calif., Jun. 16-17, 1990, Journal of the Tissue Culture Association Fields, Mumps Virus, Virology, Second Edition, pp. 989 and 993, 1990.

Primary Examiner—Douglas W. Robinson
Assistant Examiner—L. Blaine Lankford
Attorney, Agent, or Firm—David Perryman; Susan S. Rucker

[57] ABSTRACT

A method of propagating human paramyxoviruses using a continuous cell line such as NCI-H292 (HuT-292), provides a suitable alternative to MK cells for the isolation and propagation of the human paramyxoviruses.

3 Claims, No Drawings

METHOD OF PROPAGATING HUMAN PARAMYXOVIRUSES USING CONTINUOUS CELL LINES

BACKGROUND OF INVENTION

Primary rhesus monkey kidney (MK) cells have long been the cells of choice for isolation and propagation of the human paramyxoviruses: parainfluenza types 1, 2, 3, 4A, 4B, and mumps. In fact, all 5 human parainfluenzaviruses were first isolated in vervet or rhesus monkey kidney cells, and mumps-virus was initially recovered in rhesus monkeys. In addition to possessing a high level of paramyxovirus sensitivity, MK cells are particularly valuable because virus growth can be visualized in the cells both by cytopathology (CPE) and hemadsorption (HAd).

While parainfluenza types 2, and 3, and mumps viruses can be isolated in several human and simian cell lines, parainfluenza types 1, 4A, and 4B are generally recoverable only in MK cells. Thus, the use of MK cells for the isolation and propagation of human paramyxoviruses is generally advantageous; unfortunately, it is problematic as well. For example:

(a) There is only limited availability of rhesus monkeys because the trapping of these monkeys in India has recently been discouraged in order to preserve the species in its native habitat;

(b) Primates tend to carry many endogenous viruses ("adventitious agents"), e.g., adenoviruses, herpesviruses (including cytomegalovirus "CMV"), papovaviruses, myxoviruses, and enteroviruses, which increase the risk of infecting laboratory workers handling the animals and the animal tissues (The problem of workers contracting monkey B virus (*Herpesvirus simiae*), which is harmless to monkeys but is usually fatal in man, is well known.);

(c) Primary cell lines derived from the kidneys of rhesus monkeys, are sometimes latently infected with adenoviruses, enteroviruses, and herpesviruses, and almost always are infected with SV-5 (a myxovirus) and SV-40 (a papovavirus). Although these agents are not known to infect man, they often compromise virus isolation and identification, reagent production, and vaccine testing, thus constituting a major contamination problem in the laboratory;

(d) Despite the establishment of breeding colonies in the U.S., the sacrifice of monkeys for organs, such as kidneys, is generally regarded as wasteful and cruel;

(e) Monkeys are expensive to feed and house, and their use for primary cell cultures is a labor-intensive and costly endeavor.

In view of these drawbacks, the development of an alternative method for isolating and propagating human paramyxoviruses was required and sought. Until this invention, however, the alternatives suggested proved to be poor substitutes for MK cells because, inter alia, they were not as sensitive to the human paramyxoviruses as MK (e.g., Madin-Darby canine kidney ("MDCK" continuous cell line; Vero), could support the growth of no more than three serotypes of parainfluenza, and/or frequently resulted in bacterial or viral contamination (e.g., cynomolgus MK tissue culture).

SUMMARY OF INVENTION

The object of this invention is to provide a method for isolating and propagating human paramyxovirus without the use of MK cells. Consistent with this object, a method for isolating and propagating human paramyxovirus using a continuous cell line such as NCI-H292 (HuT-292), is shown herein to provide a suitable alternative to MK cells for isolating and propagating the human paramyxoviruses from clinical specimen or viral stock. Initial clinical studies also suggest that this invention can also support the primary isolation of a broad range of viruses in addition to the human paramyxoviruses, including adenoviruses, enteroviruses, rhinoviruses, herpesviruses, and some strains of influenzaviruses and respiratory syncytial virus.

DETAILED DESCRIPTION OF INVENTION

Reference will now be made in detail to the preferred embodiments of this invention. All documents cited below are specifically incorporated herein by reference.

A continuous cell line of human respiratory-tract origin was found to be a suitable alternative to MK cells for isolating and propagating the human paramyxoviruses from clinical specimens or viral stock. To achieve this goal, it was first necessary to locate candidate cell lines which exhibited the following characteristics:

(a) ready maintainability, so that adequate reserves could be frozen for future use;

(b) stability during prolonged incubation periods (paramyxoviruses being fairly slow-growing, requiring 5 to 7 days of culture to become evident);

(c) obvious virus-induced cytopathology (CPE) and, more importantly, distinctness of the host cell and nuclei from erythrocytes used in the hemadsorption (HAd) test to permit detection of the presence of virus with the same reliability as when MK cells were used; and (d) susceptibility to infection by the various strains and serotypes of the human paramyxoviruses.

In selecting the cell types to be evaluated for use in this invention, the natural pathogenesis of paramyxovirus infection in man was considered. On this basis, epithelial cells from the nose and throat were considered likely candidates, as were human lung cells. Likewise, because both human and rhesus kidney cells are sensitive to the paramyxoviruses, cell lines derived from primary or tumor cells from human or simian (monkey or ape) donors were also considered. However, only selected cells from African green (vervet) monkeys were evaluated because primary African green kidney cells are known generally to be less sensitive than MK cells for isolating paramyxoviruses. Finally, initial consideration was also given to various continuous cell lines of simian origin, including LLC-MK2, and Vero cells, as well as continuous cell lines of human origin, including A-549 cells.

Many of the candidate cell lines were ultimately found to be unsuitable for use because they exhibited poor growth characteristics and/or did not support the growth of the human paramyxoviruses. While cell lines supporting the growth of any of the six strains of human paramyxoviruses are suitable for use herein, cell lines supporting the growth of at least 4 strains are preferable, and those supporting the growth of all six strains are the most preferred.

In this regard, there did not appear to be a consistent pattern relating to which cells would exhibit poor, or no viral growth, except that parainfluenza types 1, 4A, and 4B were generally the most difficult viruses to grow in all candidate cells (even MK), while parainfluenza type 3, and mumps were the least difficult to propagate; a finding consistent with previous experience.

The poor growth characteristics of some candidate cells such as BSC-1 (a simian origin cell line), may have been due to the fact that the virus samples were subjected to such high passage levels that they had become less differentiated, and possibly had lost the specific receptor sites needed for paramyxovirus attachment. This, for instance, may account for an inability to grow parainfluenza type 4 in Vero cells; a result at odds with an earlier study (see Morimoto et al., Jpn. J. Med. Sci. Biol. 23:1-11 (1970)).

In summary, continuous cell cultures of human origin (i.e., L132, A-549, HuT-292, HEK, G-293, G-401, A-498, A-704, CAKI-1, and RD) and simian origin (i.e., LLC-MK2, BSC-1, MA-104, and Vero) were evaluated for use in the propagation and isolation of human paramyxoviruses. Suitability for use was determined based on the cell's capacity to support the growth of the human paramyxoviruses as demonstrated by CPE, HAd, hemagglutination ("HA"), and enzyme immunoassay ("EIA").

Of the cell lines evaluated (see Table 1), NCI-H292 (HuT-292) (American Type Culture Collection ("ATCC") Accession No. CRL-1848) proved to be the most sensitive, supporting the growth of all serotypes and strains of the human paramyxoviruses when used according to the present invention. (H292 cells are a relatively unknown, continuous line of mucoepidermoid carcinoma cells derived from human lung in 1985 (see Banks-Schlegel et al., Cancer Res, 45:1187-1197 (1985); Carney et al., Cancer Res. 45:2913-2923 (1985)). The cell line previously has been used for hepatitis B antigen transfection (see Yoakum et al., Science 222:385-389 (1983))). Although H292 cells generally possess excellent growth characteristics, the genetic polyploidy of the cells may limit the number of passages of usable cells.

To propagate human paramyxoviruses according to the present invention, a continuous cell line such as H292 is grown in medium containing trypsin and, optionally, insulin, transferrin, and selenium ("ITS") (Carney et al., supra). ITS was found to be unnecessary for cell maintenance or virus replication during the course of these experiments, and RPMI-1640 ("RPMI") lacking ITS proved to be satisfactory as both a growth and maintenance medium. Thus, the use of ITS in the growth and maintenance medium is optional. In contrast to ITS, trypsin is essential for the replication of paramyxoviruses in continuous cultures using either RPMI or Eagle's minimal essential medium ("EMEM") maintenance media according to the present invention.

Although MK cells do not require trypsin to support the growth of orthomyxoviruses or paramyxoviruses for example, and, when used with other viruses, the concentration required varied greatly depending on virus type, cell type, and laboratory procedure, trypsin was considered to be an important media additive. This conclusion was reached based on several studies which reported enhanced replication for many viruses after treatment with, or in the presence of trypsin, coupled with the facts that (1) influenzavirus is activated by trypsin in cells such as chick embryo, MDCK, and Vero, and (2) some paramyxoviruses are enhanced by trypsin in cultures of LLC-MK2, Vero, and HEp2 cells.

In addition to the media conditions discussed above, protocol and culture conditions were also determined which permitted the isolation and propagation of the human paramyxoviruses using a continuous cell line such as H292. This protocol includes the steps of:

a. Selecting a continuous cell line capable of supporting the growth of one or more of the human paramyxoviruses. Selection of a cell line being based on susceptibility to infection by the human paramyxoviruses as demonstrated by CPE, HAd, HA, and EIA, as well as factors such as: (a) maintainability, (b) stability during prolonged incubation periods, (c) obvious virus-induced cytopathology (CPE), and (d) distinctness of the host cell and nuclei from erythrocytes used in the hemadsorption (HAd) test;

b. Growing the cell line in a monolayer under growth medium;

c. Decanting the growth medium and rinsing the cells with maintenance medium containing trypsin (e.g., RPMI-1640 or EMEM supplemented with approximately 1.5 μg/ml trypsin or supplemented with approximately 1.5 μg/ml trypsin and approximately 0.1% ITS; see examples section of specification for discussion relating to the amount of trypsin suitable for use);

d. Inoculating the cells with clinical specimen or viral stock;

e. Adsorbing the viral particles to the cells;

f. Adding maintenance medium to the cell culture and incubating until ready for analysis, subpassaging, or harvest.

Following these procedures, the cultures may be analyzed by CPE for virus growth at intervals of approximately 2, 4, and 7 days, subpassaged to provide for maximum virus recovery (preferably 3 subpasses at weekly intervals), and hemadsorbed with guinea pig erythrocytes as described in Schmidt N. J., "Cell Culture Procedures for Diagnostic Virology," *Diagnostic Procedure for Viral, Rickettsial and Chlamydial Infections*, 6th Ed.; N. J. Schmidt and R. W. Emmons, Eds.; pp. 51-100. Am. Public Health Assoc., Wash. D.C. (1989); specifically incorporated herein by reference.

EXAMPLES

1. Viruses

Prototype strains of the human paramyxoviruses parainfluenza types 1, 2, 3, 4A, 4B, and mumps, were obtained from the reference virus collection of the Respiratory and Enteric Viruses Branch of the Center for Infectious Diseases, Centers for Disease Control ("CDC"), Atlanta, Ga. These strains are also available from the ATCC, Rockville, Md., under accession numbers VR-94, VR-92, VR-93, VR-279, VR-579, and VR-106, respectively.

In addition to the prototype strains, a total of 82 specimen isolates representing a wide time-and-place distribution also were obtained from the Respiratory and Enteric Viruses Branch of the Center for Infectious Diseases, i.e., 18 strains of parainfluenza type 1, 19 strains of parainfluenza type 2, 15 strains of parainfluenza type 3, 8 strains of parainfluenza type 4A, 4 strains of parainfluenza type 4B, and 18 strains of mumpsvirus.

Although the earliest passages of the prototype strains available were in MK cells, all but parainfluenzavirus types 4A, and 4B had been adapted to embryonated eggs. Low passage material from the egg-adapted viruses was used where possible as starting material because it was free of adventitious agents. The 82 specimen isolates had been isolated in MK cells and were stored at −100° C. thereafter.

2. Cell Cultures

The cell lines evaluated for use in the present invention are listed in Table 1. (Table 1 also provides a listing of source (tissue derivation), morphology, and karyology for each of these cell lines.) As noted, each cell line was obtained from either the CDC or the ATCC; all are available from the ATCC.

The cells were prepared weekly as tube cultures under EMEM/10% fetal bovine serum ("FBS") or EMEM/7% FBS/1% ITS growth media, for cells obtained from the CDC, or under the specialized medium recommended by the ATCC for cell lines obtained therefrom. In each study, the cells were used when the monolayers reached approximately 60-80% confluency.

3. Virus Inoculation

To inoculate each cell culture, the growth medium was decanted and the monolayer was washed once with maintenance medium. After washing, 0.2 to 0.3 ml of seed virus inoculum, or 0.3 to 0.5 ml of clinical specimen was adsorbed to the cells for about 1 hour at ambient temperature, followed by the addition of approximately 1.0 ml of maintenance medium. The tubes were then incubated at about 36° C. on a roller drum and the cultures were observed daily for CPE.

The first experiment utilized a maintenance medium consisting of Medium 199 (Gibco Laboratories, Grand Island, N.Y.) with 2% FBS (Hazleton Laboratories, Lenexa, Kans.) (previously titrated by hemagglutination-inhibition ("HI") to be free of bovine parainfluenza 3 SF4 antibodies). Later experiments employed EMEM (Flow Laboratories, McLean, Va.) supplemented with L-glutamine (Gibco Laboratories, Grand Island, N.Y.), penicillin/streptomycin, (Gibco Laboratories, Grand Island, N.Y.), 0.1% ITS (final concentrations—5 µg/ml insulin/5 µg/ml transferrin/0.005 µg/ml selenous acid; Collaborative Research, Inc., Lexington, Mass.), and 1.5 µg/ml trypsin (Sigma Chemical Co., St. Louis, Mo.). The ITS and trypsin used herein were stored in concentrated form at −70° C. The final experiments employed RPMI-1640/glutamine medium (Gibco Laboratories, Grand Island, N.Y.) with 100 U/ml penicillin, 100 µg/ml streptomycin, and 1.5 µg/ml trypsin.

Viruses were kept cold during inoculation to maintain consistency within the operation and to minimize loss of titer in the more labile viruses (i.e., parainfluenza types 4A, and 4B, and mumps).

After 7 days, the tubes were scraped and blind-passed at approximately 0.3 ml per tube (3 tubes each). Weekly intervals were chosen for subpassaging based on well-known paramyxovirus replication features and the usable lifespan of many cell cultures. At the end of each passage, one tube of each cell culture was washed with 0.01 M phosphate-buffered saline, pH 7.2 ("PBS"), and hemadsorbed with 0.4% guinea pig erythrocytes (0.2 ml of fresh cell suspension in 2.0 ml PBS, with readings taken after 15 and 45 minutes, at room temperature). The remaining two tubes were scraped, pooled (including the supernate from the first tube), and subpassaged again. Six serial passages were done, and a portion of each passage was saved at −70° C. for subsequent comparative testing to ascertain virus replication.

4. Antigen Tests

In addition to CPE and HAd, HA, EIA, and virus infectivity titrations ("IT") were also carried out on each cell culture to measure the extent of viral replication. HA titrations were performed according to standardized microtiter HA procedures, using PBS as diluent and 0.4% fresh guinea pig or human "O" erythrocytes, or 0.5% chicken red blood cells, with a 1 hour incubation at room temperature (see Hierholzer et al., Appl. Microbiol. 18:824–833 (1969)).

EIA for parainfluenza types 1, 2, and 3 was performed in polystyrene flat-bottom microtiter plates (Immulon, Dynatech Laboratories, Alexandria, Va.) coated with 75 µl of purified IgG from type-specific horse antisera according to the method of Hierholzer et al., J. Clin. Microbiol. 27:1243–1249 (1989).

EIA for parainfluenza types 4A, and 4B, and mumps was performed as above except using a biotin-avidin system (see Hierholzer et al. (1989), supra). The capture IgG was purified from guinea pig antiserum for parainfluenza 4A, ferret antiserum for type 4B, and horse antiserum for mumps. These were added at optimal dilutions as determined by checkerboard titration (see Hierholzer et al. (1989), supra) in 0.01 M carbonate buffer, pH 9.6, and incubated overnight. The plates were then washed, and viral and control antigens added, generally as noted above. After a 1.5 hour incubation at 37° C., and washing, 75 µl of the corresponding biotinylated guinea pig, ferret, or horse IgG diluted in PBS-GT (PBS-0.5% gelatin/0.15% Tween-20) was added, and the plates were incubated for an additional hour at 37° C. The remainder of the test was performed as previously described by Hierholzer et al. (1989), supra, specifically incorporated herein by reference.

Infectivity titrations were carried out as serial tenfold dilutions of virus culture made in EMEM and inoculated (0.1 ml) in quadruplicate onto appropriate cell monolayers. After a 1 hour adsorption at room temperature, 1 ml of maintenance medium was added per tube and the cultures incubated at 36° C. on a roller drum for 14 days. The titers were analyzed by CPE and HAd, and calculated by the Reed/Muench method (see Schmidt and Emmons, supra, specifically incorporated herein by reference).

5. Initial Evaluation of Cell Lines

Cell lines were chosen for initial evaluation on the basis of morphology and tissue derivation (see Table 1). Fresh tube cultures of the cells were washed once with maintenance medium (EMEM/0.1% ITS/5 µg/ml trypsin), and inoculated with the 6 prototype strains at MOIs (Multiplicity of Infections) of 0.1. The cultures were read daily for CPE. The trypsin levels initially employed (e.g., 5 µg/ml) were found to be toxic to many of the cells, so the experiment was repeated using varying doses of trypsin from 4 to 0.5 µg/ml, final concentration. In general, 1.5 µg/ml was the highest trypsin concentration tolerated by all cells.

Six sequential passages of the viruses in the cells were then made in the presence of 1.5 µg/ml trypsin, and each cell line was evaluated using CPE and HAd as indicators of virus growth, and confluency and viability as indicators of control cell health. The results of this experiment are provided in Table 2, with a "+" representing cell growth after 6 passages.

Many of the cell lines, i.e., A-549, G-401, A-498, A-704, CAKI-1, RD, and BSC-1, grew some of the viruses, but were slow to form monolayers, began sloughing after a few days in culture, or were unreadable for HAd. These were eliminated from further testing, and the remaining cells were inoculated with the paramyxoviruses in the presence of the highest level of trypsin they could tolerate. Still, the L132, HEK, Graham-293, LLC-MK2, MA-104, and all 3 Vero cell lines only supported the growth of some paramyxoviruses. Only the H292 cell line supported the growth of all 6 prototype strains. It should be noted, however, that the absence of trypsin in the medium during the adsorption/entry phase of this experiment resulted in a marked reduction in virus replication in all cells.

6. Comparison of Prototype Strains in MK and H292 Cells

The H292 cells selected according to the process described above were compared directly with MK cells in sequential passages of the prototype human paramyxovirus strains. Six passages were performed to ensure that the inoculum was diluted out so increases in antigen titer reflecting viral replication would be observed. Each antigen test was performed with all passages in both H292 and MK cells, in parallel. The comparative values for passage 6 are recited in Table 3.

Compared with MK cells, the continuous cell culture H292 was shown to:

(a) propagate all 6 paramyxoviruses to titers equivalent to those obtained in MK cells, and to higher titers than the other cell lines analyzed;

(b) be maintainable in the laboratory without special measures;

(c) produce cell monolayers that were easy to read for CPE; and (d) have a cell morphology that was distinguishable from erythrocytes in HAd tests.

7. Comparison of Wild Strains in MK and H292 Cells

The ability of the H292 cell line to support the growth of diverse paramyxovirus isolates obtained in MK cells over a 30-year period and a wide geographical spread were studied. The specimen isolates were subpassaged 6 times in H292 and MK cells, in parallel, and the passages were assayed by CPE, HAd, HA titrations, and EIA. The results are shown in Table 3 as the number of isolates recoverable at the end of 6 passages.

The strains of parainfluenza types 1, 2, and 3 were recovered in the first or second passage in both cell systems, while the strains of parainfluenza type 4, and mumps required 3 to 4 passages, as expected from the general lability of these viruses. All viruses were recovered except for 1 strain of mumps in MK cells and 2 strains of mumps in H292 cells. Thus, the H292 cells are clearly susceptible to a broad range of strains.

Moreover, a review of the diagnostic features of the different paramyxovirus serotypes in H292 cells revealed trends in the type of CPE, pattern of HAd, and titer of HA, similar to those seen in MK cells. CPE ranged from inapparent, to degenerative, to syncytial, depending on the amount of virus present, the length of culture, and the virus type. Certain virus types produced a predominantly degenerative appearance with some aggregation (e.g., parainfluenza type 1); others produced a somewhat syncytial pattern (e.g., parainfluenza types 2, and 4A). Parainfluenza type 3 produced the most recognizable syncytial CPE, and mumps was distinct in the amount of fusion produced.

Still, there was sufficient overlap in CPE descriptions between virus types and among strains of the same virus that CPE was not always a reliable predictor of virus type in H292 cells. CPE description was further confused by the relatively low degree of CPE observed, ranging from 1+(25% of the cell monolayer visibly affected) in mumps-infected cultures to 4+ (100% of cells affected) in parainfluenza type 3-infected cultures.

Hemadsorption in H292 cell cultures was similar to that seen in MK cultures. For example, parainfluenza types 1 and 2, and some cultures of parainfluenza type 3 and mumps gave uniform HAd, with the erythrocytes evenly and solidly spread over the cell monolayer, but cultures of parainfluenza type 4 and some parainfluenza type 3 and mumps gave patchy HAd patterns, usually at the edges of the monolayers. HA tests with guinea pig cells showed the same grouping of HA titers in H292 cultures as in MK cultures, with parainfluenza types 1, 2, and 3 strains typically giving the highest titers ranging from 1:8 to 1:512. Parainfluenza type 4 strains gave the lowest titers (1:1–1:16), and mumps strains gave intermediate titers of 1:4–1:64.

FA tests on virus-infected H292 cells also exhibited various staining patterns among the strains studied, as in MK cultures, but the patterns were not consistent with particular virus types. Therefore, the growth parameters observed such as variations in CPE, HAd, HA titer, and FA staining, may be suggestive of virus type but are not reliable characteristics of serotype.

The results of this comparative testing are provided in Table 4.

8. Primary Isolation in H292 Cells

A prospective comparison of H292 cells with MK cells using incoming clinical specimens was conducted, the results of which are provided in Table 5. Specimens were processed by routine procedures (see Hierholzer et al. (1989), supra), inoculated into H292 cells and MK cells, subpassaged, and tested in parallel.

For parainfluenza types 1 and 3, identical results were obtained in both cell lines, although the viruses were detected in MK cells in slightly less time than in H292 cells. For mumpsvirus, the H292 cells gave more clear CPE than MK cells, and in less time. No strains of parainfluenza types 2, 4A, or 4B were recovered from the community for evaluation during this period.

9. Production of High-Titered Stocks in H292 Cells

Stocks of the human paramyxoviruses were prepared in H292 cells and evaluated by the parameters described above, and by electron microscopy, to ascertain their usefulness as seed viruses. The results of this experiment are provided in Table 6.

The viruses were prepared as pools of infected cultures and harvested by one freeze-thaw cycle after 4 to 7 days of incubation. All of the new seed viruses were high-titered based on activity tests, consisted of typical intact paramyxovirus as determined by electron microscopy, and were devoid of bacterial, fungal, and/or mycoplasmal contamination as shown by extensive culturing. Additionally, EIA, HI, and breakthrough neutralization tests with paramyxovirus antisera showed no cross-contamination within the group or with other viruses.

The data provided in Table 6 were obtained by replicate tests on vials of virus after a total of two freeze-thaw cycles. HA and EIA titers were consistently higher on samples after multiple freeze-thaw cycles, or after storage up to 8 weeks at 4° C. These data show that virus seeds prepared in NCI-H292 cells are equal in virus titer to those formerly prepared in MK cells. Other antigen tests gave equally parallel results.

TABLE 1

Characteristics of cell lines evaluated

| Cell line* | Source | Morphology | Karyology |
|---|---|---|---|
| L-132 | embryonic lung (human) | epithelial-like | heteroploid |
| A-549 | carcinoma lung (human) | epithelial-like | heteroploid |
| NCI-H292 | carcinoma lung (human) | mucoepidermoid | polyploid |
| HEK | embryonic kidney (human) | fibroblast-like | diploid |
| Graham-293 | embryonic kidney (human) | Ad5-transformed, epithelioid | aneuploid |
| G-401 | carcinoma kidney (human) | epithelial-like | diploid |
| A-498 | carcinoma kidney (human) | epithelial-like | heteroploid |
| A-704 | carcinoma kidney (human) | epithelial-like | heteroploid |
| CAKI-1 | carcinoma kidney (human) | epithelial-like | heteroploid |
| RD | rhabdomyosarcoma (human) | mixed embryonal | heteroploid |
| MK | kidney (rhesus monkey) | mixed | normal |
| LLC-MK2 | kidney (Afr. green monkey) | epithelial-like | heteroploid |
| BSC-1 | kidney (Afr. green monkey) | epithelial-like | heteroploid |
| MA-104 | kidney (Afr. green monkey) | epithelial-like | heteroploid |
| Vero-CCL81 | kidney (Afr. green monkey) | fibroblast-like | heteroploid |
| Vero-76 | kidney (Afr. green monkey) | fibroblast-like | heteroploid |
| Vero-76/E6 | kidney (Afr. green monkey) | fibroblast-like | heteroploid |

*Cell lines were obtained from the CDC except for Vero-CCL81 cells (Accession No. CCL-81) and Vero-76 cells (Accession No. CRL-1587), which were obtained from the ATCC.

TABLE 2

Initial evaluation of cells

| | MK | LLC-MK2 | Vero 81 | Vero 76 | Vero E6 | L-132 | A-549 | NCI-H292 | HEK | G-401 | A-498 | A-704 | Caki-1 | RD |
|---|---|---|---|---|---|---|---|---|---|---|---|---|---|---|
| Para. 1 | + | − | − | + | + | − | − | + | − | − | − | − | − | − |
| Para. 2 | + | + | + | + | + | + | + | + | − | − | − | + | + | + |
| Para. 3 | + | + | + | + | + | + | + | + | + | + | − | + | + | + |
| Para. 4A | + | − | − | − | − | − | − | ± | nd | nd | nd | − | nd | − |
| Para. 4B | − | − | − | − | − | − | − | + | nd | nd | nd | nd | nd | − |
| Mumps | + | + | + | + | + | + | + | + | nd | nd | nd | + | nd | + |
| Cell Controls | OK | OK | OK | OK | OK | OK | OK | OK | OK | not OK | not OK | not OK | not OK | not OK |

+ Growth after 6 passages
− No growth
nd Not done

TABLE 3

Recovery of stored paramyxovirus isolates in MK and NCI-H292 cells

| Virus | No. of isolates | MK | H292 |
|---|---|---|---|
| Para. 1 | 18 | 18 | 18 |
| Para. 2 | 19 | 19 | 19 |
| Para. 3 | 15 | 15 | 15 |
| Para. 4A | 8 | 8 | 8 |
| Para. 4B | 4 | 4 | 4 |
| Mumps | 18 | 17 | 16 |
| Total | 82 | 81 (98.8%) | 80 (97.6%) |

TABLE 5

Primary isolate of human paramyxoviruses in NCI-H292 cells

| | No. of viruses recovered in | | Mean no. days of culture | |
|---|---|---|---|---|
| Virus | MK | H292 | MK | H292 |
| Para. 1 | 7 | 7 | 7 | 11 |
| Para. 3 | 13 | 13 | 5 | 7 |
| Mumps | 10 | 11 | 12 | 10 |

TABLE 4

Comparative growth of prototype paramyxoviruses in MK and NCI-H292 cells[a]

| | | CPE | | HAd | | HA | | EIA | | I · T (log$_{10}$) | |
|---|---|---|---|---|---|---|---|---|---|---|---|
| Virus | Strain | MK | H292 | MK | H292 | MK | H292 | MK | H292 | MK | H292 |
| Para. 1 | C-35 | 3+ | 4+ | + | + | 64 | 64 | 0.885 | 1.020 | ≧4.0 | ≧4.0 |
| Para. 2 | Greer | 4+ | 4+ | + | + | 2 | 16 | 1.485 | 1.974 | ≧4.0 | ≧4.0 |
| Para. 3 | C-243 | 1+ | 4+ | + | + | 64 | 8 | 1.522 | 1.848 | ≧4.0 | ≧4.0 |
| Para. 4A | M-25 | 2+ | 3+ | + | + | 2 | — | 0.660 | 0.497 | 4.0 | 3.5 |
| Para. 4B | 19503 | — | 3+ | — | + | — | 2 | 0.033 | 0.345 | ≦1.0 | 4.0 |
| Mumps | Enders | 1+ | 1+ | + | + | 4 | 4 | 0.641 | 0.579 | ≧4.0 | ≧4.0 |

[a]Indicators of growth after 6 passages: cytopathology (CPE), hemadsorption (HAd), and hemagglutination (HA) titer. EIA value is defined as the absorbance at 450 nm of undiluted antigen (culture supernatant) in polyclonal EIA tests (types 1–3) or biotin-avidin EIA tests (type 4 and mumps). Infectivity titer is the log$_{10}$ TCID$_{50}$ per ml at 7 days.

TABLE 6

Growth parameters of human paramyxovirus seed stocks prepared in NCI-H292 cells

| | | CPE | HAd[a] | HA titers[b] | | | EIA titer[c] | Infectivity[d] | |
|---|---|---|---|---|---|---|---|---|---|
| Virus | Strain | degree/type | g. pig | chick | g. pig | human | | MK | H292 |
| Para. 1 | C-35 | 2+/degen./aggreg. | u | 32 | 512 | 512 | 3.0 | 6.5 | 6.5 |

TABLE 6-continued

| Growth parameters of human paramyxovirus seed stocks prepared in NCI-H292 cells | | | | | | | | | |
|---|---|---|---|---|---|---|---|---|---|
| | | CPE | HAd[a] | HA titers[b] | | | EIA | Infectivity[d] | |
| Virus | Strain | degree/type | g. pig | chick | g. pig | human | titer[c] | MK | H292 |
| Para. 2 | Greer | 3+/variable/syncyt. | u | 32 | 256 | 64 | 4.5 | 6.5 | 6.2 |
| Para. 3 | C-243 | 4+/degen./syncyt. | u/p | 1 | 256 | 128 | 3.5 | 7.8 | 7.7 |
| Para. 4A | M-25 | 1+/variable/syncyt. | p | 1 | 8 | 1 | 2.0 | 5.7 | 5.5 |
| Para. 4B | 19503 | 1+/variable/aggreg. | p | 1 | 8 | 1 | 1.0 | 3.7 | 3.7 |
| Mumps | Enders | 1+/fusion/sync./degen. | u/p | 16 | 64 | 16 | 2.5 | 6.7 | 7.3 |

[a]u Uniform, p patchy hemadsorption at 30 minutes, 23° C.
[b]HA titer is the reciprocal of the highest dilution of antigen (culture supernatant) exhibiting complete agglutination with chicken, guinea pig, and human "O" erythrocytes in 1 hour at ambient temperature
[c]EIA titers are noted as the $\log_{10}$ of the highest dilution of antigen that exhibits a P/N (positive/negative) value of ≧3.0
[d]Infectivity titers are noted as the $\log_{10}$ $TCID_{50}$ per ml after 14 days of incubation in roller culture at 36° C.

We claim:

1. A method for propagating mammalian paramyxovirus selected from the group consisting of type 1, 2, 3, 4A, 4B and mumps comprising the steps of:

a. growing NCI-H292 cells;

b. inoculating the cells with paramyxovirus; and c. harvesting the paramyxovirus.

2. NCI-H292 cells infected with a human paramyxovirus.

3. NCI-H292 cells infected with a human paramyxovirus selected from the group consisting of parainfluenza type 1, 2, 3, 4A, 4B, and mumps.

* * * * *